(12) United States Patent
Maciunas et al.

(10) Patent No.: US 7,616,735 B2
(45) Date of Patent: Nov. 10, 2009

(54) TOMOSURGERY

(75) Inventors: Robert Maciunas, Chesterland, OH (US); David Dean, Shaker Heights, OH (US); Xiaoliang X. H. Hu, New York, NY (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 11/728,927

(22) Filed: Mar. 27, 2007

(65) Prior Publication Data

US 2007/0286343 A1    Dec. 13, 2007

Related U.S. Application Data

(60) Provisional application No. 60/786,457, filed on Mar. 28, 2006.

(51) Int. Cl.
*G21K 5/10* (2006.01)
(52) U.S. Cl. .......................... 378/69; 378/65
(58) Field of Classification Search .................. 378/65, 378/69; 600/425, 427
See application file for complete search history.

(56) References Cited

U.S. PATENT DOCUMENTS

| | | | |
|---|---|---|---|
| 5,802,136 A * | 9/1998 | Carol | 378/65 |
| 6,385,286 B1 * | 5/2002 | Fitchard et al. | 378/65 |
| 6,504,899 B2 * | 1/2003 | Pugachev et al. | 378/65 |
| 6,735,277 B2 * | 5/2004 | McNutt et al. | 378/65 |
| 7,027,557 B2 * | 4/2006 | Llacer | 378/65 |
| 7,289,599 B2 * | 10/2007 | Seppi et al. | 378/65 |
| 7,302,038 B2 * | 11/2007 | Mackie et al. | 378/69 |

* cited by examiner

*Primary Examiner*—Edward J Glick
*Assistant Examiner*—Thomas R Artman
(74) *Attorney, Agent, or Firm*—Kragul Jac + Kalnay, LLC

(57) ABSTRACT

Systems, methods, and other embodiments associated with Tomosurgery are described. One method embodiment includes logically dividing a target volume into treatment slices to be radiated individually by co-planar beams. The method embodiment also includes planning a two dimensional path for moving a shaped isocenter through a treatment slice where the isocenter is produced by the intersection of the co-planar beams. The method embodiment also includes planning a three dimensional path for moving the shaped isocenter through the target volume based, at least in part, on two dimensional paths. The method provides a signal to control a radio surgery device to deliver radiation using the coplanar beams to the target volume based, at least in part, on the three dimensional path.

34 Claims, 6 Drawing Sheets

TOMOSURGERY

CROSS REFERENCE TO RELATED APPLICATIONS

This application claims the benefit of U.S. Provisional Application 60/786,457 titled Tomosurgery, filed Mar. 28, 2006, which is incorporated herein.

COPYRIGHT NOTICE

A portion of the disclosure of this patent document contains material subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

Radiosurgery has typically been performed using a step-and-shoot approach that delivers radiation according to a three dimensional plan of multiple three dimensional shots. Multiple shots are usually required to destroy the target pathology. Step and shoot dose delivery involves repositioning the patient outside of the irradiation field to reposition the centroid of the conformal radiation dose. This type of radiosurgery has been time consuming and may in some cases have produced sub-optimal results.

Radiosurgery may be performed using various devices. For example, Leksell (Elektra, Stockholm, Sweden) provides a Gamma Knife™ which may be referred to as an LGK. The LGK provides accurate stereotactic radio surgical brain lesion treatment. The LGK derives its therapeutic radiation from 201 60Co radiation sources. A patient is exposed to these sources through pluggable collimator channels. The radiation beams passing through unplugged collimator channels focus in the center of a collimator helmet to create an elliptically shaped conformal dose distribution. LGK shots are traditionally elliptical due to the general shape of the human skull. For a single shot, dose drop-off is steep at the boundaries of this ellipse (e.g., 90% to 20% isodose). However, dose drop-off steepness is diminished and made difficult to estimate when two or more shots have overlapping dose distributions.

Shot planning seeks to achieve desired lesion coverage and killing. However, shot packing is not as simple as filling a tumor, a theoretical bag, with ellipses of dose. Planning multiple shots is difficult due to the consequences of unintended intersections of beams from different shots. These unintended intersections of beams from different shots complicate treatment planning, and thus lengthen the time required to plan a multi-shot treatment. Furthermore, shot packing approaches typically cannot commence until the entire pre-planning images are acquired.

Planning and delivery complexity are related to the geometric complexity and volumetric complexity of a target volume. For example, large lesion volume, complex lesion shape, and/or complicated geometric relationships between the lesion and critical structures complicate planning, and thus increase planning time and increase the likelihood that suboptimal results will occur.

Conventional LGK treatment planning begins with a treatment planning team that includes, for example, a neurosurgeon, a radiation oncologist, and a radiation physicist. The treatment planning team may survey pre-radio surgical images (e.g., CT, MR) to locate the lesion in a series of adjacent 2D image slices. Drawing the boundary of the lesion is referred to as "segmentation". Other objects of interest, (e.g., critical structures near the lesion), may also be segmented at this time. Segmentation is typically performed manually using a contour drawing tool. Shot packing strategies may not begin until the entire set of image slices is available.

Conventional treatment planning falls into two categories: forward treatment planning, and inverse treatment planning, with forward treatment planning being the standard of care as of 2007. Treatment planning begins with known parameters including prescribed dose, lesion location, segmented tissue object contours, and so on. Forward planning includes a trial-and-error approach for choosing shot parameters including number of shots, shot positions, collimator sizes, shot weights, and so on. As shot parameters are selected the treatment planning team can calculate and evaluate the sum of the radiation dose distribution. The treatment team will then manually adjust setup parameters until an "acceptable" treatment plan is obtained. This is an extremely technical and manual process requiring the input of several highly skilled personnel. This approach is not deterministic.

Given time limitations imposed by single session treatment a significant issue for forward treatment planning is the relative size of the search and solution space for acceptable treatment plans. For a small lesion with a simple shape, forward planning may perform adequately. The treatment planning team may place a shot in the center of the target volume and then gradually add extra shots to fill the under-dosed regions closer to the lesion surface. However, the treatment plan search space increases dramatically when a lesion has a large target volume, a complex target shape, and/or a complex geometric relationship between the target volume and nearby critical section (CS). In this situation, treatment planning may require hours to obtain an acceptable treatment plan. The shots resulting from this trial-and-error procedure may produce unintended radiation dose overlap, particularly when multiple shots are placed in close proximity.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Figure 1:
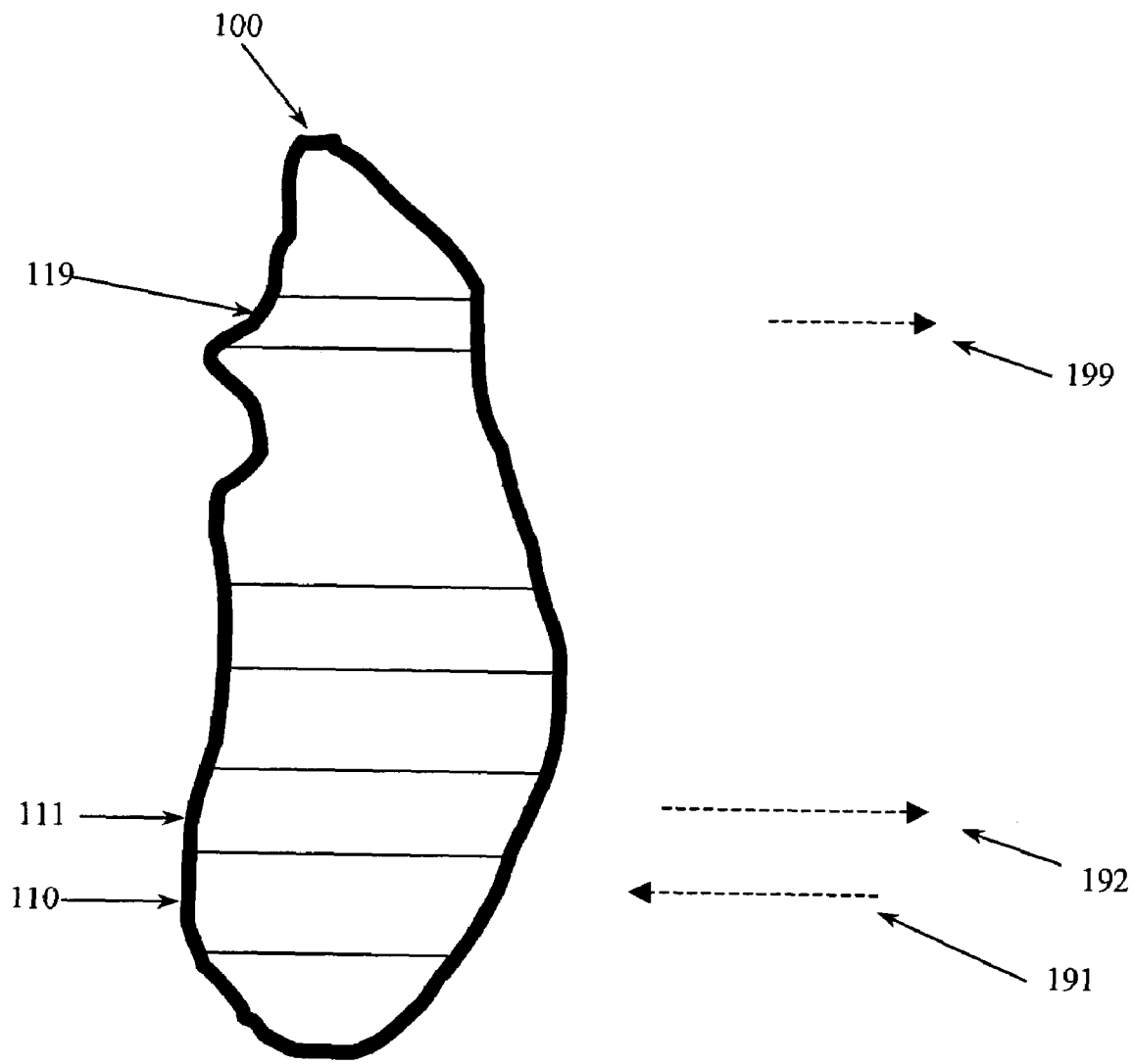
FIG. 1 illustrates a portion of a three dimensional target volume divided into a set of two dimensional treatment slices, which may also be referred to as scanning planes.

In one embodiment Tomosurgery involves slice based radiosurgery that includes moving a high-precision, controlled-shaped isocenter between scan points along a set of scanning lines in a portion of a target volume divided into sets of treatment planes. In one example, the scan points may be visited in a raster-scanning pattern controlled by a set of 2D plans. Scan points may also be visited slice by slice through a target volume as controlled by a 3D plan built from the set of 2D plans. The slice thickness may be optimized to smooth peak-to-peak transitions between slices. Shot weight can be adjusted by controlling parameters including, but not limited to, shot movement speed, shot movement location, the number of beams being used in the shot, the distance of the radiation source from the target volume, and the size of beams used in the shot. The number of beams and the size of the beams may be determined by controlling on-the-fly collimator changes (e.g., plug pattern, plug size), and/or by controlling a radiation source position. The location of the isocenter can be moved by controlling parameters including, but not limited to, the number of different beams being used, temporal delays between beams, delivery apparatus location and/or orientation, radiation source location, and/or orientation, and patient location and/or orientation.

Tomosurgery seeks the precise and complete destruction of a chosen target without significant unintended and/or unanticipated concomitant damage to adjacent tissue. The radiation used in Tomosurgery is ionizing high-energy beams that provide sufficient energy to cause electrons to escape from the outer shell of atoms in the target structure. The ionizing high-energy beams may radiate from, for example, $^{60}$Co. Cell death or injury may result from DNA, cell membrane, and/or organellar damage.

Tomosurgery planning may include a two stage optimization where 2D slices are solved and then a 3D assembly of 2D slices is solved. To solve slices, the planning systems and methods need to have slices. Thus, the 3D target volume is first identified and then partitioned into 2D slices. The 3D target volume may be identified from images including, for example, MR images, CT images, PET images, SPECT images, X-rays, and so on. The 3D target volume may then be logically "cut" into smaller pieces. In one example, the smaller pieces are "slices" that can be considered to be two dimensional surfaces over which a shot isocenter can be passed. The 2D surfaces may be treated as a set of scan points lying in the same plane. The 2D projection images may be used to determine the placement of raster lines that connect scan points and thus control desired dose distribution in the first-stage optimization.

On these 2D projection images, tumor and CS regions may overlap. Therefore, in one example, a set of rules may be used to control placement of raster lines on a raster-scan plane. The rules may include placing parallel raster lines sequentially along the y direction, locating discrete scan points of each raster line only within the tumor region in the corresponding projection image, and not locating any discrete scan point within the projected CS region. Using these rules facilitates determining the coordinates (x, y, z) of the discrete scan points making up raster lines. In one example, the final treatment plan is made up of a series of scan points assigned with the optimized weight as controlled, for example, by the speed of the moving shot.

While a "slice" is actually a three dimensional volume, it may be treated as a two dimensional surface formed of a set of scan points for planning and treatment purposes. In one example, multiple slice orientations may be considered to provide multiple options for solving the set of 2D problems. Additionally, in one example, combinations of orientations may be considered to provide even more options for solving the set of 2D problems. For example, a first portion of a target volume may be sliced in a first orientation while a second portion of a target volume may be sliced in a second orientation. Solving slices arranged in different orientations may be computationally expensive but may provide superior results for target volumes that have particularly complicated geometries and/or that interact with (e.g., wrap around) critical structure (CS) in geometrically complex ways.

Tomosurgery may involve both parallel planning and parallel delivery. Individual slices may be solved in parallel and may be solved according to different strategies simultaneously. For example, solutions that apply different importance functions and different scanning patterns may be solved simultaneously so that different options are available to attempt to solve the final 3D assembly. Additionally, different solutions that involve delivering a dose as a disk, an ellipse, or as another shaped shot may also be computed in parallel to make even further options available for the final 3D assembly. Additionally, different solutions that involve controlling dose (in)homogeneity may be solved in parallel to provide even further options for the final 3D assembly. Finally, multiple 3D assemblies may be computed in parallel and an optimal solution can be selected from the available plans. Different plans may be more deliverable using different delivery devices. Thus, part of the final 3D planning solution may include selecting a delivery device for the plan. For example, a first 3D plan may be optimized using a first delivery device (e.g., LGK) while a second 3D plan may be optimized using a second delivery device (e.g., medical LINAC).

Reduction to 2D slices and parallel delivery may be possible since delivery apparatus (e.g., LGK) may be adaptable to provide a substantially continuous dose using substantially coplanar beams and/or sets of substantially coplanar beams. Using substantially coplanar beams may facilitate reducing unintended beam intersections which may in turn facilitate both simplifying planning and delivering therapy in parallel.

Example systems and methods may perform intensity modulated radiation therapy (IMRT) by modulating the speed of a moving shot or moving shots. Dose can be controlled by how long a shot lingers in a certain location. In one example, the moving shot(s) may be disk-shaped, though other shot shapes may be employed. IMRT may rely on achieving relative motion between a patient and a radiation field to provide a planned radiation dose in a continuous fashion. The relative motion may be achieved by moving the patient, by moving the delivery apparatus, by moving the radiation source, and by combinations thereof.

While some example systems and methods are described in association with an LGK, the systems and methods are not so limited. For example, treatment planning and radio-surgery may be associated with other delivery mechanisms and radiation sources including, for example, a cyberknife having a single point source of radiation, a C arm linear accelerator, an apparatus having multi-leaf collimators (MLC), and so on.

Similarly, while example systems and methods are described in connection with brain surgery, the systems and methods are not so limited. For example, treatment planning and radiosurgery may be applied to other body parts including, for example, the torso, extremities, and so on. Additionally, while the examples are described in terms of human treatment, radiosurgery may be performed on additional subjects (e.g., dogs, horses, cows).

Additionally, while example systems and methods describe a raster based approached associated with a moving shot, it is to be appreciated that other motion patterns may be employed. Raster based approaches may simplify mechanical adaptations to conventional apparatus and may facilitate simplifying motion plan computations. However, in some examples, other motion plans (e.g., helical, spiral) for the moving shot may be employed.

In one embodiment, an LGK shot delivery mechanism dynamically moves a shot isocenter to control dose homogeneity and/or dose inhomogeneity. In one embodiment, an LGK plug-pattern that facilitates selectively blocking collimators on an LGK helmet is used. For example, all the collimators except those on a single layer (e.g., lowest layer, most nearly coplanar row) are blocked. This facilitates producing substantially coplanar beams. Thus, a focused isocenter dose profile can be produced within a narrow plane. The patient and/or field can be moved to make the plane correspond to one of the 2D planes for which a raster plan has been computed. The "shot" created by this plug-pattern may be a disk-shaped distribution of lethal radiation (e.g., a shot).

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

The following includes definitions of selected terms employed herein. The definitions include various examples and/or forms of components that fall within the scope of a term and that may be used for implementation. The examples are not intended to be limiting. Both singular and plural forms of terms may be within the definitions.

"Machine-readable medium", as used herein, refers to a medium that participates in directly or indirectly providing signals, instructions and/or data that can be read by a machine (e.g., computer). A machine-readable medium may take forms, including, but not limited to, non-volatile media (e.g., optical disk, magnetic disk), and volatile media (e.g., semiconductor memory, dynamic memory). Common forms of machine-readable mediums include floppy disks, hard disks, magnetic tapes, RAM (Random Access Memory), ROM (Read Only Memory), CD-ROM (Compact Disk ROM), and so on.

"Data store", as used herein, refers to a physical and/or logical entity that can store data. A data store may be, for example, a database, a table, a file, a list, a queue, a heap, a memory, a register, a disk, and so on. In different examples a data store may reside in one logical and/or physical entity and/or may be distributed between multiple logical and/or physical entities.

"Logic", as used herein, includes but is not limited to hardware, firmware, executing instructions, and/or combinations thereof to perform a function(s) or an action(s), and/or to cause a function or action from another logic, method, and/or system. Logic may include a software controlled microprocessor, discrete logic (e.g., application specific integrated circuit (ASIC)), an analog circuit, a digital circuit, a programmed logic device, a memory device containing instructions, and so on. Logic may include a gate(s), a combinations of gates, other circuit components, and so on. Where multiple logical logics are described, it may be possible in some examples to incorporate the multiple logical logics into one physical logic. Similarly, where a single logical logic is described, it may be possible in some examples to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, or other means that can be received, transmitted and/or detected.

"Software", as used herein, includes but is not limited to, one or more executing computer instructions that temporarily transform a general purpose machine into a special purpose machine. Software causes a computer, processor, or other electronic device to perform functions, actions and/or behave in a desired manner. Software may be embodied in various forms including routines, algorithms, modules, methods, threads, and/or programs. In different examples, software may be implemented in executable and/or loadable forms including, but not limited to, a stand-alone program, an object, a function (local and/or remote), a servelet, an applet, instructions stored in a memory, part of an operating system, and so on. In different examples, computer-readable and/or executable instructions may be located in one logic and/or distributed between multiple communicating, co-operating, and/or parallel processing logics and thus may be loaded and/or executed in serial, parallel, massively parallel and other manners.

"User", as used herein, includes but is not limited to, one or more persons, software, computers or other devices, or combinations of these.

Some portions of the detailed descriptions that follow are presented in terms of algorithm descriptions and representations of operations on electrical and/or magnetic signals capable of being stored, transferred, combined, compared, and otherwise manipulated in hardware. These are used by those skilled in the art to convey the substance of their work to others. An algorithm is here, and generally, conceived to be a sequence of operations that produce a result. The operations may include physical manipulations of physical quantities. The manipulations may produce a transitory physical change like that in an electromagnetic transmission signal.

It has proven convenient at times, principally for reasons of common usage, to refer to these electrical and/or magnetic signals as bits, values, elements, symbols, characters, terms, numbers, and so on. These and similar terms are associated with appropriate physical quantities and are merely convenient labels applied to these quantities. Unless specifically stated otherwise, it is appreciated that throughout the description, terms including processing, computing, calculating, determining, displaying, automatically performing an action, and so on, refer to actions and processes of a computer system, logic, processor, or similar electronic device that manipulates and transforms data represented as physical (electric, electronic, magnetic) quantities.

FIG. 1 illustrates a portion 100 of three dimensional target volume that has been logically partitioned into a set of two dimensional treatment slices. In one embodiment, Tomosurgery involves continuously delivering a radiation dose with dynamic intensity modulation performed temporarily, spatially, or both in accordance with a 3D plan derived from a set of 2D plans developed for the set of treatment slices. The radiation may be delivered to a set of scan points arranged along a set of scan lines (e.g., 191, 192, . . . 199) that correspond to treatment lines 110, 111, . . . 119 in portion 100. The spatial intensity modulation may be achieved by moving the center of a shot, which may be achieved by causing relative motion between a patient, a delivery apparatus, and/or a radiation source.

In one embodiment, a continuous LGK shot delivery mechanism may dynamically move a shot isocenter to control dose homogeneity. The LGK may be configured to deliver dose continuously with a modulated shot radiation dose level moving at modifiable speeds along suitable pathways in accordance with the set of 2D plans to improve both dose conformality and normal tissue sparing. The 2D plans may be solved independently and in parallel to reduce planning time. The 2D planning problems may include varied-speed shot movement to improve dose conformality.

The 2D plans may then be assembled into a 3D plan. Once again, segments of the 3D plan can be assembled in parallel. Consider a 3D volume sliced into 256 2D slices for planning. In one example, some or all of the 256 2D slices may be solved in parallel. Additionally, some or all of the 256 2D slices may be solved using different parameters (e.g., importance functions, scan plans). Plans for the 256 2D slices may then be assembled into a 3D plan. Once again, multiple 3D plans may be computed in parallel and a most optimal solution chosen at the end. In one example, 16 separate process may be tasked with assembling sets of 16 slices in parallel. In another example, 128 process may assemble sets of adjacent slices, then 64 processes may assemble sets of four slice assemblies, and so on. Larger subsets of slices may then ultimately be assembled into the final 3D model.

With one 3D plan made up of multiple 2D slices, in one example radiation may be delivered to treat different slices in parallel. Parallel radiation delivery within isolated treatment slices facilitates reducing therapy delivery time. Improvements in dose conformality and homogeneity may also improve radiosurgery for larger-volume and/or more geometrically complex lesions.

Example systems and methods may control a delivery apparatus to produce a disk-like shot using a delivery apparatus that produces a nearly planar dose. These systems and methods may rely on a kinetic equation that describes a "3D dose bar" radiation distribution when this disk-like shot moves through a lesion in each treatment slice in, for example, a raster scanning fashion.

Example systems and methods may consider the characteristics of the 3D dose bar, consider the interaction between adjacent 3D dose bars in the same slice (e.g., inter-raster line dose), and consider the interaction between two slices (e.g., inter-slice dose). Example systems and methods may also consider dose interaction and inhomogeneity resulting from changing dose bar velocity. Example systems and methods may use information concerning disk-like shot radiation dose distribution to automatically generate an inverse treatment plan that includes modulated velocity.

In one example, Tomosurgery inverse treatment planning involves a two-stage optimization strategy utilizing an importance-weighted quadratic objective function and iterative least-square minimization. The resulting delivery causes a shot to move continuously through a target volume (e.g., lesion) delivering tumoricidal radiation to a series of adjacent slices in a raster-scan format. So long as relative motion between the target volume and the irradiation field is possible, continuous motion of the radiation dose is possible.

The inverse treatment planning is to be performed in a clinically relevant and acceptable time frame to provide improved plan quality and application to different radiation therapy modalities. Moving the high-precision shaped isocenter relies on being able to produce relative motion between a target volume and an irradiation field. The relative motion may be achieved using positioning units associated with the patient, the delivery apparatus, the radiation source, and so on. For example, equipping an LGK with two positioning units, each of which has three computer controlled motors, may facilitate continuously changing the position of the shot isocenter.

As described above, pre-operative 3D MR-scanning, LGK treatment planning, and LGK radiosurgery may need to be accomplished in a single work session. Thus, time is of the essence. The single session is conventionally mandated because the rigid stereotactic frame is affixed to a patient's skull. This fixed length of time may lead to compromises between manual treatment planning and the radiosurgery procedure in complex cases. While conventional systems tend to wait until the entire 3D MR-scan is complete, some example systems can start solving some individual 2D slices as soon as they are available, further reducing overall planning and thus session time. In some cases, 3D pre-operative imaging, tomosurgery planning, and radiation delivery may be separated into different sessions that do not need to be completed in a single session by the use of fiducials that may be affixed to the target volume and/or to anatomy that will maintain a constant relationship to the target volume in between imaging, planning, and delivery. For example, a set of three fiducials that are highly visible to MR imaging may be affixed to a patient skull in a pre-determined pattern and used subsequently in planning and/or delivery.

For a treatment slice, the central transverse plane may be referred to as the "raster-scan plane" in which the disk-shaped shot moves in a raster format. The treatment slices may have an optimal slice thickness. In one example, the slice-scan nature of the Tomosurgery paradigm is understood by analyzing dose distribution for a constant-speed moving disk-shaped shot in the form of linear scan, single-plane raster scan and multi-plane raster scan. Analyzing dose distribution by linear scan (moving shot along a straight line) facilitates obtaining the optimal slice thickness. Analyzing single-plane and multi-plane raster scans facilitates understanding dose distribution, including approximated dose drop-off steepness and isodose contour width. The following discussion illustrates the analysis.

In one example, a disk-shaped shot is generated using a helmet plug-pattern having the upper four layers of a commercially available collimator closed with only a fifth layer open. This approximates coplanar beams. In the example, the voxel size of the 161×161×161 3D matrix that stores the dose kernel is 0.25×0.25×0.25 $mm^3$. Different dose kernels for available collimator sizes (e.g., 4 mm, 8 mm, 14 mm, 18 mm) may be calculated. In one example, a 4 mm collimator is used since smaller shots increase the likelihood of achieving greater dose conformality.

Given a disk-shaped dose kernel matrix d and a moving speed related variable v(x) at the location x, a dose distribution D due to a linear scan along the x axis can be expressed according to:

$$D(x, y, z) = d \otimes \frac{1}{v} = \sum_{x'} d(x - x', x, y, z)(1/v(x')) \quad (1)$$

where $\otimes$ is the convolution operator. For disk movement performed with discrete steps, v(x) is a shot-weight series. In one example, the speed may be treated as a constant and the $^{60}$Co can be assumed not to decay. In this example, equation (1) simplifies to:

$$D(x, y, z) = \sum_{x'} d(x - x', y, z) \quad (2)$$

If the straight line along which the disk-shaped shot moves is considered to be infinitely long, then the example can ignore the regions close to the start and end points. Therefore, D can be treated as a bar-shaped compressed cylinder and the dose profile on a cross-sectional plane (y-z) of the 3D dose bar will be the same, (e.g., $D(x_1, y, z) = D(x_2, y, z)$ for arbitrary $x_1$ and $x_2$). Therefore, the cross-sectional dose profile of the 3D dose bar can be denoted as $D_{cs}(y, z)$ for purposes of simplification.

Given $D_{cs}(y, z)$ as the cross-sectional dose profile of the 3D dose bar, define $D_{cs}(y=0, z)$ as the function $\phi$, which is approximately symmetrical by $z=0$. In one embodiment, planning may depend on previously determining the similarity between $\phi$ and $D_{cs}(y, z)$ at arbitrary y fixed and determining the optimal offset for two shifted $\phi$ functions so that their summation has the flattest/smoothest peak-to-peak transition. For the sum of two shifted bell-shaped functions, such as F(x)+F(x+offset), the peak-to-peak transition represents the curve between the peaks of F(x) and F(x+offset).

Because the correlation coefficient is independent of origin and scale, it may be used to evaluate the similarity of $D_{cs}(y, z)$ to $\phi$ at different fixed y. The correlation coefficient has the value between 0 and 1. The complete correlation has the correlation coefficient equal 1.

The pre-determining may include searching for an optimal offset for which the sum of two shifted $\phi$ functions has the smoothest peak-to-peak transition. Given two shifted $\phi$ functions, $\phi(z)$ and $\phi(z-l_o)$, define $H_{l_o}(z)$ as:

$$H_{l_o}(z) = c \cdot \Phi(z) + \Phi(z - l_o), c \in [0.5, 1] \quad (3)$$

where c is a constant and $l_o$ is the offset between those two shifted $\phi$ functions. When c equals 1, a horizontal line from peak to peak ($z \in [0, l_o]$) is desired to present the most smoothness. When c is less than 1, a non-horizontal straight line is expected to ideally reach the most smoothness. To quantify the smoothness, define the smoothness as the average of the unsigned curvature of the given curve segment (peak-to-peak transition). The unsigned curvature $\kappa$ in this case can be given as:

$$\kappa(z) = \left| \frac{\frac{\partial H_{l_o}(z)}{\partial^2 z}}{\left(1 + \left(\frac{\partial H_{l_o}(z)}{\partial z}\right)^2\right)^{3/2}} \right| \quad (4)$$

The predetermining may also include calculating $\kappa$ in discrete form. By focusing on peak-to-peak smoothness for a particular region (e.g., the curve segment of $H_{l_o}(z)$ when $0 \leq z \leq l_o$), the peak-to-peak smoothness $C_s(l_o)$ can be presented as the arithmetic mean of the curvature in discrete:

$$C_s(l_o) = \frac{1}{N} \sum_{i=1}^{N} \kappa_i \quad (5)$$

where the peak-to-peak curve segment of $H_{l_o}(z)$ is represented by N discrete points. Because the curvature measures the failure of a curve to be a straight line and the curvature of a regular straight vanishes if that straight line is not horizontal, the smoothest peak to peak transition will be obtained when $C_s(l_o)$ tends to zero.

The predetermining may also include analyzing 3D dose bars derived from clinical cases. The analysis may include searching the optimal offset $l_o$ where $C_s(l_o)$ is minimum for different c value in $H_{l_o}(z)$, such as c=0.5, 0.6, 0.7, 0.8, 0.9, and 1. The shot dose kernel matrix used has the voxel size at 0.25×0.25×0.25 mm$^3$.

In one example system, the planar raster scan may be performed on a transverse plane (x-y). A single-plane raster scan may be made up of multiple parallel linear scans on the same plane. A multi-plane raster scan can be formed from a stack of single-plane raster scans. While a single-plane raster scan is described, it is to be appreciated that other scanning patterns may be employed (e.g., spiral, helical).

The cross-sectional dose profile $D_{cs}(y, z)$ of a single 3D dose bar is approximately mirror-symmetrical along either z or y axis. The minimal and mean correlation coefficient is no less than 0.977 and 0.991 respectively. Therefore, $D_{cs}(y, z)$ has substantially the same function form as $\phi$ at any y value, but different scale. Thus, $D_{cs}(y, z)$ can be expressed at arbitrary y as:

$$D_{cs}(y, z) = D_{cs}(y, 0) \cdot \Phi(z), \text{ at arbitrary } y \quad (6)$$

The single-plane raster scan can be regarded as the alignment of multiple parallel 3D dose bars centered by the same plane in a raster format where each raster line is the axial of the respective 3D dose bar. Dose distribution delivered by a single-plane raster scan can be approximated as a sum of multiple $\phi$ functions with varied scale along any longitudinal line (parallel with z axis) in dose space regardless of inter-raster line distance. Assume the single-plane raster scan has N raster lines and the inter-raster line distance is $l_a$. The dose distribution for this single-plane raster scan on a cross-sectional plane can be presented as $D_{sps}(y, z)$:

$$D_{sps}(y, z) = \sum_{n=1}^{N} D_{cs}(y + (n-1) \cdot l_a, z) \quad (7)$$

$$= \sum_{n=1}^{N} D_{cs}(y + (n-1) \cdot l_a, 0) \cdot \Phi(z)$$

-continued $$= \Phi(z) \sum_{n=1}^{N} D_{cs}(y + (n-1) \cdot l_a, 0)$$

Note that $D_{cs}(y+(n-1)\cdot l_a, 0)$ is a constant. Therefore, for the single-plane raster scan the dose profile along a longitudinal line $D_{sps}(y,z)$ at arbitrary y fixed, will reserve the function form of $\phi$ but has varied scale determined by:

$$\sum_{n=1}^{N} D_{cs}(y + (n-1) \cdot l_a, 0).$$

In one example, an optimal offset for $\phi$ may exist. In the provisional application, this optimal offset was seen at 4.01 mm. Even while c in the $H_{l_o}$ function was not 1, the optimal offset was still 4.01 mm. Thus, the optimal offset value may be universally valid so that the smoothest dose transition by the multi-plane raster scan along any longitudinal line can be reached if the treatment slice thickness equals the optimal offset. Therefore, by choosing the treatment slice thickness to be the same as the optimal offset, a multi-plane raster scan in the raster format by a disk-shaped shot will generate smooth dose transition around treatment slice junctions instead of unexpected dose overlapping due to hard-to-predict beam intersections/overlapping, and divide the lesion into the least number of treatment slices without sacrificing dose homogeneity inside the lesion.

In the experiments described in the provisional application, the FWHM values (4.01 mm) were close to the optimal offset values for all cases and therefore may be used to approximate the optimal treatment slice thickness directly. $H_{l_o}$ may be defined as a weighted sum of two shifted $\phi$ functions corresponding to the scenario with the two raster lines per single-plane raster scan instead of multiple shifted $\phi$ functions associated with the more general cases with several raster lines per single-plane raster scan. For multiple shifted $\phi$ functions with the same optimal offset value the overlapped dose will still have the smooth/flat transition from peak to peak since $\phi$ has the very steep drop-off so that one $\phi$ function has minimal impact on another $\phi$ function that is far enough away.

A lesion volume might not be exactly divided by the optimal treatment slice thickness, leaving a portion of a lesion undivided. When the offset value $l_o$ increases outside a pre-defined range, the profile of $H_{l_o}$ between the peaks of two overlapped $\phi$ functions varies from a hill to a platform and then to a valley. If the optimal offset value cannot be used, then a smaller $H_{l_o}$ is favored because a larger $H_{l_o}$ may lead to under-dosed peak-to-peak transition.

Example systems and methods may use single-plane raster scanning to create elliptical isodose contours on cross-sectional planes. Example systems and methods may then extend to multi-plane raster scanning by stacking multiple single-plane raster scans. Example systems and methods may rely on the dose overlapping effect in situations where one treatment slice is smaller than another. This facilitates creating a dose conformal to the lesion volume if the cut-off cross-sectional geometrical shape of a lesion has continuous and roughly 1$^{st}$ order linear change within a pre-defined thickness. Therefore, example systems and methods may consider the dose distribution on the mid-plane of a treatment slice, which can be planned as a 2D problem. After assembling (e.g., stacking) individually planned treatment slices, the overlapped dose from slice to slice will conform to the lesion geometric changes from one treatment slice to another. Therefore, the original 3D planning problem is converted to a series of 2D planning problems that can be individually solved without 3D convolution, which means planning time can be reduced. Planning time can be reduced even further because the individual 2D planning problems may be solved in parallel and planning may begin even before the entire 3D MR image is acquired. 2D solutions may then be stacked into the 3D plan, with the stacking occurring in parallel. In some examples, different approaches to solving the individual 2D planning problems may be undertaken in parallel with optimal solutions being selected from the results of the different approaches. Similarly, different approaches to solving the 3D assembly problem may be undertaken in parallel with an optimal solution being selected from the different solutions.

Example systems and methods may consider how isodose contours vary while applying different scan formats. The number of single-plane raster scans affects the width of isodose contours along the longitudinal z direction only. Thus, stacking multiple single-plane raster scans having an optimal treatment slice thickness does not worsen the dose spread-out within each treatment slice itself and will proportionally expand isodose contours/surfaces along longitudinal z direction. Therefore, single-plane raster scanning can be seen as individually filling a dose within a corresponding treatment slice.

In example systems and methods, modulating shot speed facilitates improving conformality of the dose to the target lesion. In example systems and methods, a Tomosurgery treatment plan includes a series of raster lines that include a series of discrete scan spots/stops where the moving shot will stay. A time-factor is assigned to a scan spot and represents how long the moving shot takes passing through. Assuming an undecayed radiation source, this time-factor is analogous to shot weight.

In one example, Tomosurgery treatment planning first determines the location of a series of adjacent treatment slices that cover the entire lesion volume. Second, the 3D volumes for tissue types (e.g., lesion, CS, normal tissue (NT)) within each treatment slice are projected to the central transverse plane of that treatment slice. In one example, the disk-shaped Tomosurgery shot dose profile at ≧50% isodose is approximately the same thickness as each treatment slice and therefore the treatment plan can be solved for a 2D projection view of each treatment slice. Thus, 2D plan optimizations involve 2D convolution, which can be performed more quickly than 3D convolution. Third, the 3D dose distribution of optimized 2D plans are calculated. These 3D dose distributions are assembled (e.g., stacked) longitudinally to create the final 3D plan.

Example systems and methods may consider how to orient treatment slices. It is computationally simplest if the treatment slices are parallel to the original MR-based x-y plane. In this case treatment slice thickness can be measured along the longitudinal z axis. The lesion thickness may, or more likely may not be fully divisible by the optimal treatment slice thickness.

A 2D plan may manage a single-plane raster scan by the moving disk-shaped shot. Dose level in each treatment slice may increase slightly after the 3D treatment plan is directly assembled. A target volume (e.g., lesion) may not be exactly divisible into slices of the optimal thickness. Thus, there may be a remaining undivided portion of target volume thickness. Therefore, example systems and methods may organize an additional treatment slice that covers the undivided lesion portion that is partially overlapping with the first or the last slice previously divided out. For these two partially overlapped slices, assembling the corresponding 2D plans will not yield a smooth/flat peak to peak transition.

In some examples, treatment slices may have a transverse (x-y) orientation, the same orientation as an original MR slice data. Other example systems and methods are not so limited. In one example, a target volume may be serially sectioned into treatment slices along the pre-determined longitudinal z direction. The central transverse plane of a treatment slice is referred to as "raster-scan plane" onto which the disk-shaped moving shot may be aligned.

Given an overall tumor volume thickness T along the longitudinal direction (e.g., the z direction) and an optimal treatment slice thickness $T_{opt}$, the division of the tumor volume can be determined, in one example, using the following expression:

$$T = T_{opt} \times N + R \quad (3\text{-}1)$$

There are two possible situations: 1) R=0, where T can be exactly divided by $T_{opt}$ and 2) R≠0, where T cannot be exactly divided by $T_{opt}$ and the remaining undivided portion of the tumor volume has a thickness<$T_{opt}$. For both of these situations, the corresponding central transverse planes of the initial N treatment slices may be chosen as the raster-scan planes so that the distance between two adjacent raster-scan planes is $T_{opt}$. If the tumor volume is completely filled by these treatment slices (R=0), the procedure can conclude. If the tumor volume can not be filled completely (R≠0), an extra raster-scan plane (N+1$^{th}$) may be appended. However, the distance between the last two raster-scan planes (N$^{th}$ and N+1$^{th}$) is R instead of $T_{opt}$. In an example described in the provisional application, $T_{opt}$ is 4 mm for the use of a 4 mm collimator. It is to be appreciated that for other collimator sizes other optimal slice thicknesses may be employed. For the raster-scan planes, a serial raster line may be used as the path for the moving disk-shaped dose.

In one example, $z_s$, the position of a raster-scan plane is recorded along the z direction. The volumes of different tissue types within the range of $z_s \pm X$ mm may be projected onto the corresponding raster-scan plane. These 2D tissue projections are used to determine the desired dose distribution in the first-stage optimization. The 2D projections of both the tumor and CS may be saved separately while the regions without tumors or CS may be regarded as NT. Overlap of the 2D tissue projections for tumors and CS is possible in some situations. Given the 2D tissue projection for a raster-scan plane, the rules described above can be applied to place the raster lines. The rules facilitate determining the coordinates (x, y, z) of these scan points making up the raster lines.

Using a disk-shaped dose kernel and a set of scan points representing the raster lines, the resulting dose can be calculated using:

$$D^d = d * \tau \Rightarrow D^d(x, y) = \sum_m \sum_n d(m - x, n - y) \tau(m, n) \quad (3\text{-}2)$$

where τ represents a time series variable that represents the time it takes the "moving shot" to pass through a "unit length" of each raster line. More specifically, τ is the shot weight in the terminology of the conventional LGK, and, finally, d is the disk-shaped shot dose kernel.

In one example, both optimization stages may use a similar quadratic objective function and importance-weighted iterative least-square minimization. Adjustment of the prescribed dose or the importance factors can push a treatment plan via this optimization towards a desired result. In one example, the prescribed dose for each case may be adjusted to control the average dose in the entire tumor volume. The importance ratio may be emphasized to match planned dose distribution to desired dose distribution for one (e.g., tumor only) or two (e.g., tumor plus CS) tissue types.

An importance-weighted objective function may be used to solve for τ:

$$O(\bar{\tau}) = \sum_{tissue} \sum_i I_i (D_i^p - D_i^d)^2 = \sum_{tissue} \sum_i I_i \left( D_i^p - \sum_j d_{ij} \tau_j \right)^2 \quad (3\text{-}3)$$

where $D_i^p$ is the prescribed dose for the tumor, NT, and CS, $D_i^d$ is the planned dose distribution to be optimized, $d_{ji}$ of the dose kernel represents the dose contribution to the i$^{th}$ spatial location while the shot moves through the j$^{th}$ scan point. Because the slice information may be projected to the corresponding raster-scan plane, the dose calculation at this stage is a 2D convolution operation that uses the central transverse plane of $d_{ji}$. $I_i$ is the predefined importance factor of each tissue type assigned to the i$^{th}$ spatial location. The projection results in tumor and CS may overlap and thus there may be a location on a 2D projection where both a tumor and a CS appear. Therefore, one example may treat the cost of Eq. (3-3) as the sum of the contributions from all three tissue types. Eq. (3-3) is a convex problem that may be solved using an iterative least-square minimization based on the following iterative equation:

$$\tau_j^{k+1} = \tau_j^k \left( \sum_{tissue} \sum_i I_i \cdot d_{ji} \cdot D_i^p \right) \cdot \left( \sum_{tissue} \sum_i I_i \cdot d_{ji} D_i^{d(k)} \right)^{-1} \quad (3\text{-}4)$$

The solution space search is guided by an "update" factor that is the ratio between the prescribed dose and the calculated dose from the previous iteration.

In one example, it may be possible to fix the normalized prescription dose to 0.8 for tumor, 0.2 for NT, and 0.2 for CS. Given n 2D treatment plans produced by the first-stage optimization, the assembly of the final 3D plan dose distribution ($D_f$) is performed by weighting these n 2D plans according to:

$$D_f = \sum_n w_i \cdot D_i^s \quad (3\text{-}5)$$

where $D_i^s$ is the 3D dose matrix saving the dose distribution by the i$^{th}$ single-plane raster scan (e.g., the 2D treatment plan), and is calculated based on Eq. (3-2); $w_i$ is the weight assigned to the i$^{th}$ single-plane raster scan and the variable to be solved by the second-stage optimization. If $w_i=1$, there is no adjustment to the i$^{th}$ planar scan. A large change of $w_i$ from 1 means that there is a large adjustment.

The dose distribution for a single-plane raster scan has steep dose drop-off along the longitudinal z direction. Therefore, one example may limit the thickness of the dose matrix $D_i^s$ to $3 \times T_{opt}$ to save computation time. An importance-weighted objective function similar to Eq. (3-3) and an iterative equation similar to Eq. (3-4), derive the second stage optimization presented in Eqs. (3-6) and (3-7), respectively:

$$O(\overline{w}) = \sum_{tissue} \sum I \cdot (D_f^P - D_f^d)^2 = \sum_{tissue} \sum I \cdot \left(D_f^P - \sum_{N+1} w_i D_i^s\right)^2 \quad (3\text{-}6)$$

$$w_i^{k+1} = w_i^k \left(\sum_{tissue} \sum_{N+1} I \cdot D_i^s \cdot D_f^P\right) \cdot \left(\sum_{tissue} \sum_{N+1} I \cdot D_i^s D_f^{d(k)}\right)^{-1} \quad (3\text{-}7)$$

where l is the importance factor assigned to each tissue type; w is a vector of size n, the number of the 2D treatment plans. In this second-stage optimization, one example may fix the normalized tolerance dose at 0.2 for NT, and adjust the prescription dose for tumor tissue virtually by a trial-and-error approach that depends on both tumor volume and whether CS is present. Adjustment away from the prescribed tumor dose may occur as a trade-off between in-tumor average dose and dose conformality. A highly conformal dose in a small tumor may be closer to the original prescribed dose (e.g., relatively higher) than in a large tumor. In one example, the importance ratios of tumor:NT:CS may be set the same in the second-stage optimization as in the first-stage. After the second-stage optimization, the time-series τ of each 2D treatment plan may be adjusted by multiplying the corresponding weight $w_i$ in order to get the final, optimized, 3D LGK Tomosurgery treatment plan.

In one example, the first-stage optimization of each 2D slice treatment plan can be limited to a pre-determined, configurable number of iterations (e.g., 50). In one example, second stage weight adjustments may be made. A large weight adjustment may occur on the last two 2D treatment plans because of the partial overlap of the last two treatment slices, and a small weight adjustment may occur on the treatment slices nearest the tumor central transverse plane. To get the final 3D plan, τ of each 2D treatment plan may be multiplied by the corresponding weight $w_i$.

In one example, second-stage optimization may be limited to a pre-determined, configurable number of iterations (e.g., 5). A smaller number of iterations may be employed since complex 3D convolution calculations may be reduced. This also provides treatment planning time improvements over conventional methods.

After first-stage optimization, the time-series τ is extended (e.g., the shot lingers) near the tumor boundary and smoothly decreases its value (e.g., increases the speed) as the disk-shaped shot progresses toward to the tumor center. Also, the optimal value of τ tends to be less variable in this central area. The optimization algorithm seeks to match the planned dose distribution to this desired flat dose distribution. Near the tumor boundary, the reduction in adjacent raster lines results in reduced, dose contributions. As a result, raster lines near the tumor boundary optimally have a boosted dose that compensates for the reduction in adjacent scan lines. In the center of the tumor, raster lines have a similar number of nearby scan lines. Thus τ is approximately constant to create the desired constant dose distribution by the optimization. Each optimized single-plane raster scan by the corresponding 2D plan has the desired flat "dose pie" enclosed by the 50% prescription isodose surface.

The second-stage optimization may adjust 2D treatment plans during the 3D plan assembly. The last two slices (e.g., end slice and next to end slice) often have the scanning planes closer to each other than the other adjacent slices and thus the dose transition between them has a higher amplitude with a hill profile. Dose weighting adjustments are determined by factors like the total length of each raster line in the current treatment slice and in the nearby treatment slices, the longitudinal position of each raster-scan plane, and the number of all raster-scan planes.

The tumor prescription dose may be changed in the second-stage optimization so that the average in-tumor dose is not too high. Making modest changes in the prescribed dose during the optimization facilitates improving dose homogeneity and/or conformality. Dose conformality and CS survival may be closely coupled since they may be mutually exclusive goals.

Tomosurgery may employ various delivery apparatus that produce high-accuracy focal radiation dose delivery in the form of a moving, disk-shaped isocenter that results from the intersection of multiple beamlets. The apparatus may employ a rigid yet mobile frame-based patient localization device supporting dynamic dose delivery via a moving isocenter. In one example, an existing LGK may be modified.

One example platform includes a medical Linac™ (Varian Associates, Palo Alto, Calif.) mounted with a multi-leaf collimator (MLC). The Peacock™ system (NOMOS Corporation, Sewickley, Pa.) is one commercially available, MLC-mounted system. The Linac can shape radiation to a slit (fan) beam. The platform may include an optional ring-shaped secondary helmet with multiple collimator channels through which multiple beams can focus to an isocenter mimicking an LGK Tomosurgery disk-shaped shot, and a high-accuracy robotic positioning system that connects a head frame to the ring-shaped secondary helmet.

In one example, a delivery apparatus could include a secondary helmet that includes a solid bowl or cylindrical tube with a ring-shaped base. This secondary helmet may be placed on a high-precision computer-controlled rotary table, so that it can rotate with an expected, controllable angular velocity. The base of the rotary secondary helmet may have multiple collimator channels that shape radiation beams received from an externally slit beam into multiple temporally delayed small beamlets. These beamlets, which may be temporally delayed due to the rotation of the helmet, focus to create a disk-shaped isocenter dose. A stereotactic (head) frame may be attached to this helmet through an automatic phantom positioning system similar to the APS of the LGK model C.

Example systems and methods may interact with a calibration unit. In a polymer gel-MRI dosimeter, a polymer gel may be formulated by dispersing monomer into an aqueous gel matrix. Irradiated polymer gel will present a different T2 relaxation rate than non-irradiated polymer. Therefore, following irradiation, a T2-weighted 3D MR image of the gel-based phantom may be used to report the absorbed dose distribution. For a specific gel formulation, the relationship between absorbed dose distribution and R2 (1/T2) weighted map may be assumed to be linear within a suitable range. Compared with other radiosurgery/radiotherapy dosimeters, the polymer gel-MRI method provides high resolution 3D dose distribution data. Once a polymer gel-MRI dosimeter has been calibrated, it can be used to verify the dose delivery accuracy of a Tomosurgery procedure. To increase the co-registration accuracy of the treatment plan and the dosimeter 3D MR image of the delivered dose, multi-modality fiducial markers may be employed.

PABIG (polyethylene glycol diacrylate, N,N'-methyl-enebisacrylamide, gelatin) gel formulation may be used with the dosimeter. An MR-scan of the irradiated gel-based phantom may use a volume selective 32-echo Carr-Purcell-Meiboom-Gill pulse sequence (e.g., TE1, TE2, . . . , TE32=40 ms, 80 ms, . . . , 1280 ms, TR of 2.3 s, reconstructed voxel size of 1×1×1 mm$^3$) with phase encoding being applied in two orthogonal directions and Fourier interpolation taking place in the slice reconstruction direction. The readout T$_2$ matrix includes the reconstructed slices converted to an R$_2$ (1/T$_2$) matrix. The calibration curve of the PABIG gel preparation is obtained by linearly fitting R$_2$ values in the dose range of 0-35 Gy through the following equation:

$$R_2(D)=\alpha D+R_2(0) \quad (5\text{-}1)$$

where α is the dose sensitivity value and D is the dose level. Then, the calibration curve is normalized. The dose delivered to the phantom may be obtained using the same MRI pulse sequence.

Dosimetry may include acquiring two images, a pre-operative (e.g., pre-irradiation) and a post-operative (e.g., post-irradiation) MRI scan of the phantom. The pre-operative MRI scan may be performed by using a spoiled T$_1$-weighted 3D-fast field echo (FFE) sequence. The pre-operative MRI image may be input to the treatment planning algorithm which simulates the Tomosurgery procedure. The post-operative MRI scan may be based on the same MRI sequence used in the gel-MRI dosimeter calibration scan. The MRI readout may be converted to a R$_2$ matrix and then converted to a normalized dose (percentage) based on the calibration curve.

To deliver radiation to an isocenter with an accurate distribution and weight, an apparatus may include a portion that rotates continuously with a known, controllable, angular velocity. A fixed slit beam (20 cm×2 cm) may irradiate the rotating secondary ring collimator with the phantom attached internally. In one example, delivering x-y planar symmetrical radiation at each isocenter may be simplified by using a 360 degree rotation of the collimator helmet with a constant angular velocity. Given fixed Linac output power, and a constant angular velocity for the rotary collimator helmet, the dose rate detected at the isocenter may be deterministic. The radiation beams passing through the collimator channels of the secondary helmet may be analyzed and characterized using a gel-MRI dosimeter. Then, a dose kernel calculation model may be used to match the setup. Then, the relationship of the delivered isocenter dose rate to the angular velocity of the rotary helmet may be obtained. The knowledge of this relationship (ref. Eq. (5-2)) facilitates transferring the Tomosurgery treatment plan to other dose delivery plans.

Based on the Tomosurgery treatment planning algorithm described above, a final treatment plan may be made up of a series of scan points assigned with the optimized weight (speed). Given fixed Linac output power, the shot moving speed (weight) may be converted to the corresponding angular velocity of the rotary helmet based on the simplified equation:

$$\omega_i = \frac{2\pi}{D_d/\eta(w_i)} \quad (5\text{-}2)$$

where $\omega_i$ represents the angular velocity of the rotary helmet to deliver the isocenter shot to the i$^{th}$ scan point; w is the weight (shot speed) assigned to a scan point; η is a function of w describing the dose rate converted from the shot speed; and, D$_d$ is the desired dose to be delivered. For this simplified equation, factors and coefficients relevant to the radiation physics is implicitly modeled by the function η. The model η and the dose kernel calculation model may be specific to the radiation source and the secondary helmet design.

To translate the Tomosurgery paradigm to the LGK, there are at least two options: 1) replacing the original manufacturer components with an automatic positioning system based on a pair of Cartesian robots; or 2) not only changing the positioning system, but also changing the secondary helmet and the placement of radiation sources. In one example, only the fifth-layer collimator channels (44 totally corresponding to 44 Cobalt-60 sources) are opened. Thus, the dose rate is lower than that of a plug pattern with all collimator channels (201 totally) opening. The dose rate could be increased if a customized secondary helmet was used. Thus, it may be possible to increase the number of or change the shape of collimator channels in a customized secondary helmet. The number of Cobalt-60 sources could also be increased. Note that the collimator orientation of the current secondary helmet does not allow beamlets to conform in a coplanar fashion. Therefore, in one example, in an LGK dedicated to Tomosurgery, the number of Cobalt-60 sources may be increased and the secondary collimator helmet may be modified to provide only coplanar radiation beams.

Motorized control of a multi-leaf blocker (MLB) may be implemented using a series of parallel leaves that may be individually controlled. These leaves may slide in/out to turn on/off an underneath collimator channel on-the-fly during the treatment delivery, allowing for more flexible dose shaping (e.g., conformality). Thus, a computer-controlled MLB system may allow more complex treatment delivery including dose shaping and steeper dose drop-off, thereby significantly reducing the dose to which normal and critical structures would be exposed. An automated MLB may provide on-the-fly collimator diameter shifts while being assisted by correctly positioning the main body of the secondary helmet.

Figure 2:
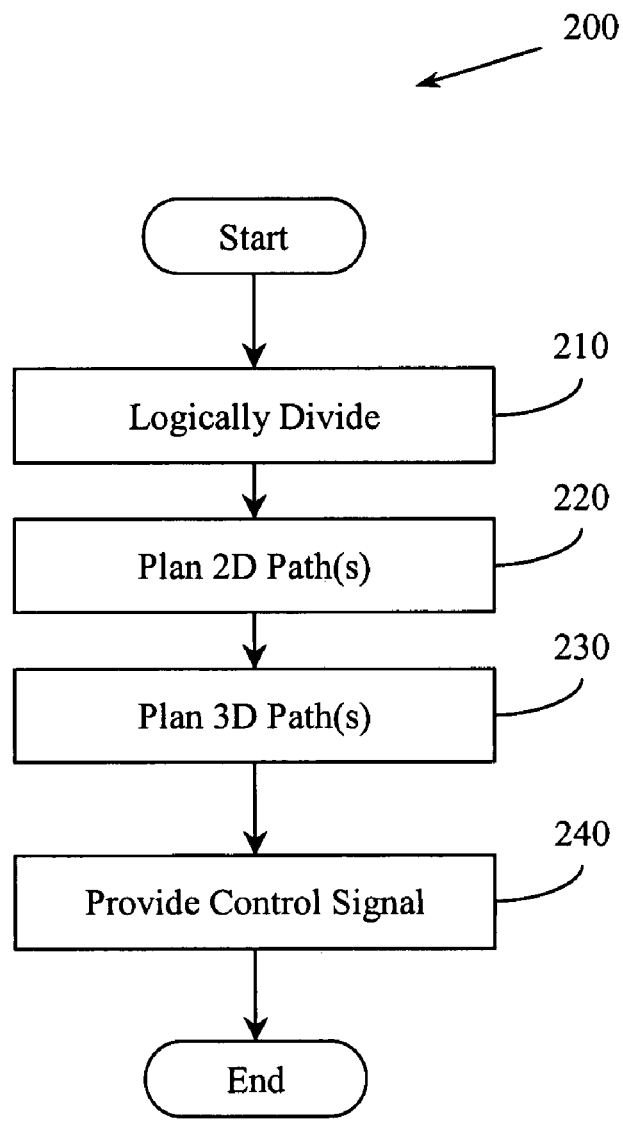
FIG. 2 illustrates an example method associated with radiosurgery planning.
Figure 3:
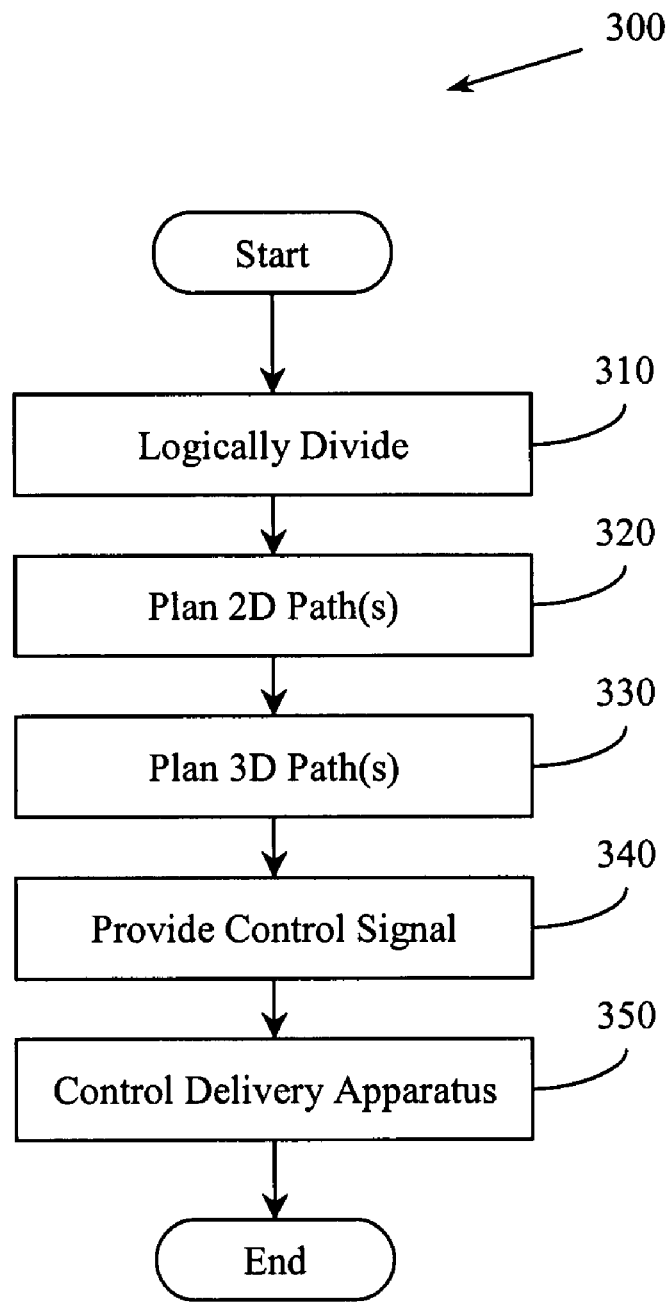
FIG. 3 illustrates an example method associated with radiosurgery planning and delivery.

Having described the science and engineering of Tomosurgery, the following description of the figures illustrate example methods and systems for planning and performing Tomosurgery. FIG. 2 illustrates an example method 200 associated with Tomosurgery planning. FIG. 3 illustrates an example method 300 associated with Tomosurgery planning and delivery.

Example methods may be better appreciated with reference to flow diagrams. While for purposes of simplicity of explanation, the illustrated methods are shown and described as a series of blocks, it is to be appreciated that the methods are not limited by the order of the blocks, as in different embodiments some blocks may occur in different orders and/or concurrently with other blocks from that shown and described. Moreover, less than all the illustrated blocks may be required to implement an example method. In some examples, blocks may be combined, separated into multiple components, may employ additional, not illustrated blocks, and so on. In some examples, blocks may be implemented in logic. In other examples, processing blocks may represent functions and/or actions performed by functionally equivalent circuits (e.g., an analog circuit, a digital signal processor circuit, an application specific integrated circuit (ASIC)), or other logic device. Blocks may represent executable instructions that cause a computer, processor, and/or logic device to respond, to perform an action(s), to change states, and/or to make decisions. While the figures illustrate various actions occurring in serial, it is to be appreciated that in some examples various actions could occur concurrently, substantially in parallel, and/or at substantially different points in time.

Method 200 may include, at 210, logically dividing a target volume to be radiated into treatment slices. These treatment slices may then be individually radiated. In one example, before logically dividing the target volume into treatment slices, method 200 will determine a treatment slice thickness.

Method 200 may also include, at 220, planning a two dimensional path for moving a shaped isocenter through a treatment slice. The isocenter will be produced at the intersection of co-planar beams. Since a target volume may be divided into a set of treatment slices, the planning at 220 may occur for multiple slices. In one example, the shaped isocenter for which the path will be planned will have a disk shape. In one example, the two dimensional path will include a set of scan points to be visited by the isocenter. In one example, the two dimensional path will be a raster scan path. In one example, planning a two dimensional path through a treatment slice includes calculating a resulting dose according to equations described above. Similarly, planning a two dimensional path through a treatment slice may include solving for $\tau$ according to equations described above.

Method 200 may also include, at 230, planning a three dimensional path for moving the shaped isocenter through the target volume based, at least in part, on two or more of the two dimensional paths. In one example, a shot weight produced by the coplanar beams is modulated by controlling the movement of the isocenter. In addition to moving the isocenter, shot weight may be modulated by controlling one or more of, a number of coplanar beams applied to the target volume, a hole size in a collimator through which at least one of the coplanar beams is to pass, and a temporal delay between one or more of the coplanar beams applied to the target volume. In one example, assembling the three dimensional plan may include solving for a final three-dimensional plan dose according to equations described above.

Method 200 may also include, at 240, providing a signal to control a radiosurgery device to deliver radiation using the coplanar beams to the target volume based, at least in part, on the three dimensional path. Providing the signal may include, for example, generating an interrupt, sending a data packet, controlling the voltage on a control line, providing a file that includes path data, providing executable instructions, and so on.

In one example, two dimensional paths through treatment slices are to be planned substantially in parallel. In one example, two dimensional paths through different treatment slices may differ in at least one of, scan pattern, importance weighted quadratic objective function, and slice orientation. Additionally, in one example, planning a first two dimensional path through a first treatment slice may begin before a second treatment slice has been defined. The three dimensional plan may reveal issues that went unobserved during two dimensional planning. Thus, method 200 may also include changing a tumor prescription dose between planning two dimensional paths and planning the three dimensional path.

In one example, method 200 may also include receiving a pre-operative image(s). The pre-operative image may include a representation of at least a portion of the target volume. Thus, the logical dividing at 210 may include analyzing the pre-operative images. The pre-operative images may be, for example, magnetic resonance images, computed tomography (CT) images, x-ray images, and so on.

Method 300 may include some actions similar to those described in connection with FIG. 2. For example, method 300 may include the logical dividing at 310, the 2D path planning at 320, the 3D path planning at 330, and providing a control signal at 340. However, method 300 may also include additional actions.

Consider that the delivery apparatus may be dynamically controllable. Control may be exercised for example, over radiation source distance, over the number of collimator openings, over the size of collimator openings, and so on. In one example, control may be done on-the-fly. Thus, method 300 may include, at 350, controlling a delivery apparatus to deliver a set of coplanar beams according to the three dimensional plan. Controlling the delivery apparatus may include, for example, controlling the delivery apparatus to deliver the coplanar beams to two or more treatment slices substantially in parallel. Controlling the delivery apparatus may also include, for example, controlling the opening and closing of collimator holes, controlling the angular velocity of a rotating radiation source, controlling the angular velocity of a rotating blocking device, and so on.

The delivery apparatus may provide radiation from radiation sources. Radiation sources may decay over time. Therefore, to improve treatment, method 300 may also include calibrating the delivery apparatus before controlling the delivery apparatus to deliver the radiation using the coplanar beams. With the calibration data acquired, method 300 may also include controlling the delivery apparatus based, at least in part, on the calibration. Calibrating the delivery apparatus may include, for example, acquiring a signal from a polymer gel-MRI dosimeter to which the delivery apparatus applied a set of coplanar beams.

Method 300 may also include, in one example, selecting a delivery apparatus to deliver the coplanar beams based, at least in part, on the three dimensional plan.

Method 200 and/or method 300 may also include fixing a fiducial marker(s) at a position relative to the target volume. Thus, pre-operative images will include representations of the fiducial markers. Alternatively, method 200 and/or method 300 may simply include receiving pre-operative images that include representations of the fiducials. With the fiducials placed and visible, assembling the three dimensional plan may depend, in one example, on a relationship between an image of a fiducial in a first treatment slice and an image of a fiducial in a second treatment slice. Similarly, with the fiducials placed and visible, control of the delivery device may depend, at least in part, on determining a relationship between a portion of the target volume and another item (e.g., a collimator opening, a radiation source). Use of these fiducials may free example systems from constraints associated with fixed stereotactic frames and/or single session imaging/planning/delivery.

While FIGS. 2 and 3 illustrates various actions occurring in serial, it is to be appreciated that various actions illustrated in these figures could occur substantially in parallel. By way of illustration, a first process could logically divide a target volume, a second process could perform 2D planning and a third process could perform 3D planning. While three processes are described, it is to be appreciated that a greater and/or lesser number of processes could be employed and that lightweight processes, regular processes, threads, and other approaches could be employed.

Figure 4:
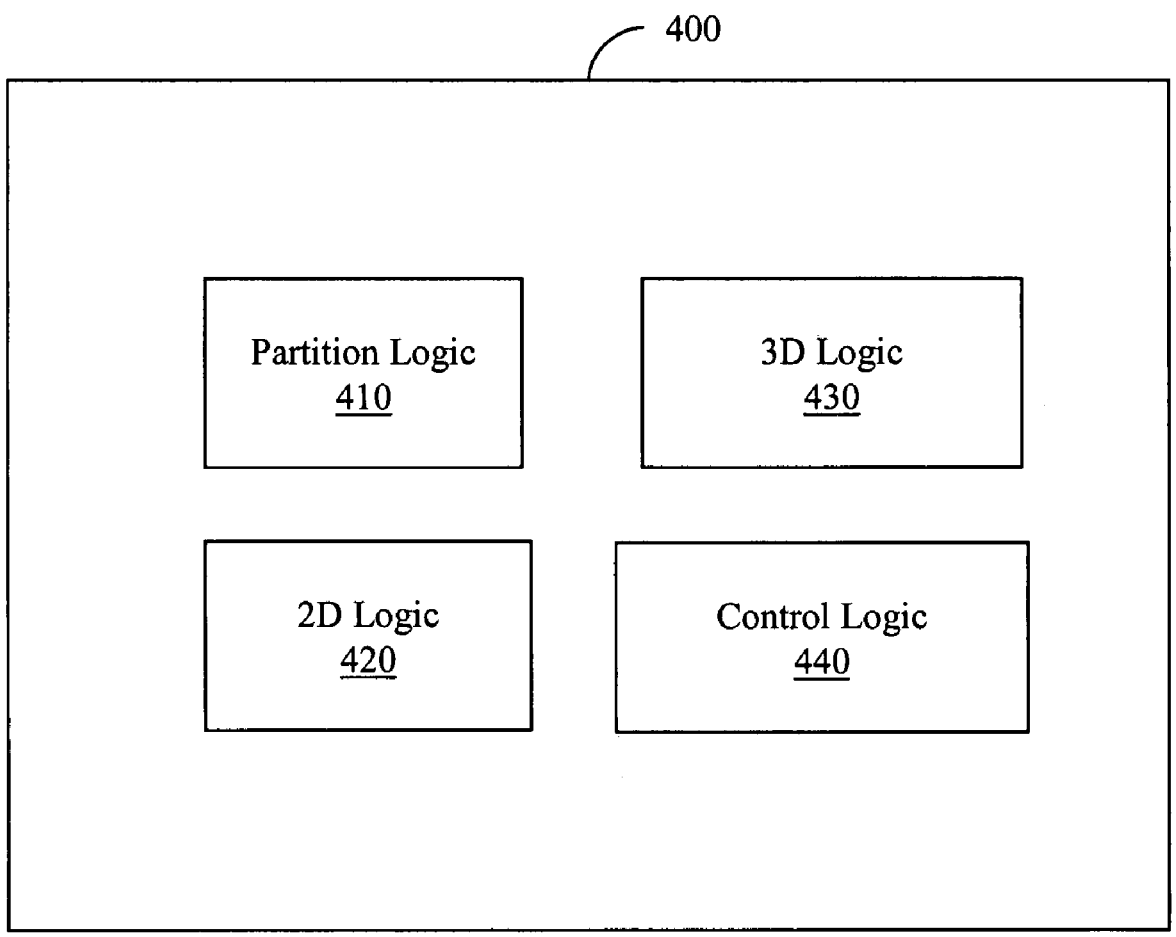
FIG. 4 illustrates an example apparatus associated with radiosurgery planning.

FIG. 4 illustrates an example apparatus 400 associated with Tomosurgery planning. Apparatus 400 may include a first logic (e.g., partition logic 410) to logically partition a target volume into a set of treatment slices. The target volume represents a tissue to be subjected to radiation surgery. The radiation may be delivered by a set of coplanar beams. The radiation may be delivered from fixed radiation sources and/or from radiation sources that may move (e.g., circularly) about a target volume.

Apparatus 400 may also include a second logic (e.g., 2D logic 420) to determine a set of two dimensional raster scanning paths through the set of treatment slices. The determining may proceed in accordance with the methods and equations described above. The determining may account for whether the path is to be created from fixed radiation sources and/or from moveable (e.g., rotating) sources.

Apparatus 400 may also include a third logic (e.g., 3D logic 430) to determine a three dimensional plan to irradiate the target volume to within a pre-determined dose. As described above, the three dimensional plan is to be based, at least in part, on the set of two dimensional raster scanning paths. Once again the determining may account for whether the path is to be created from fixed radiation sources and/or from moveable (e.g., rotating) sources. Apparatus 400 may also include a fourth logic (e.g., control logic 440) to control a delivery apparatus to deliver radiation in a set of coplanar beams to the target volume. The delivery will be made in accordance with the three dimensional path. The control logic 440 may generate a set of signals that are provided to a delivery apparatus. The signals may take different forms, though an electrical signal is preferred.

Figure 5:
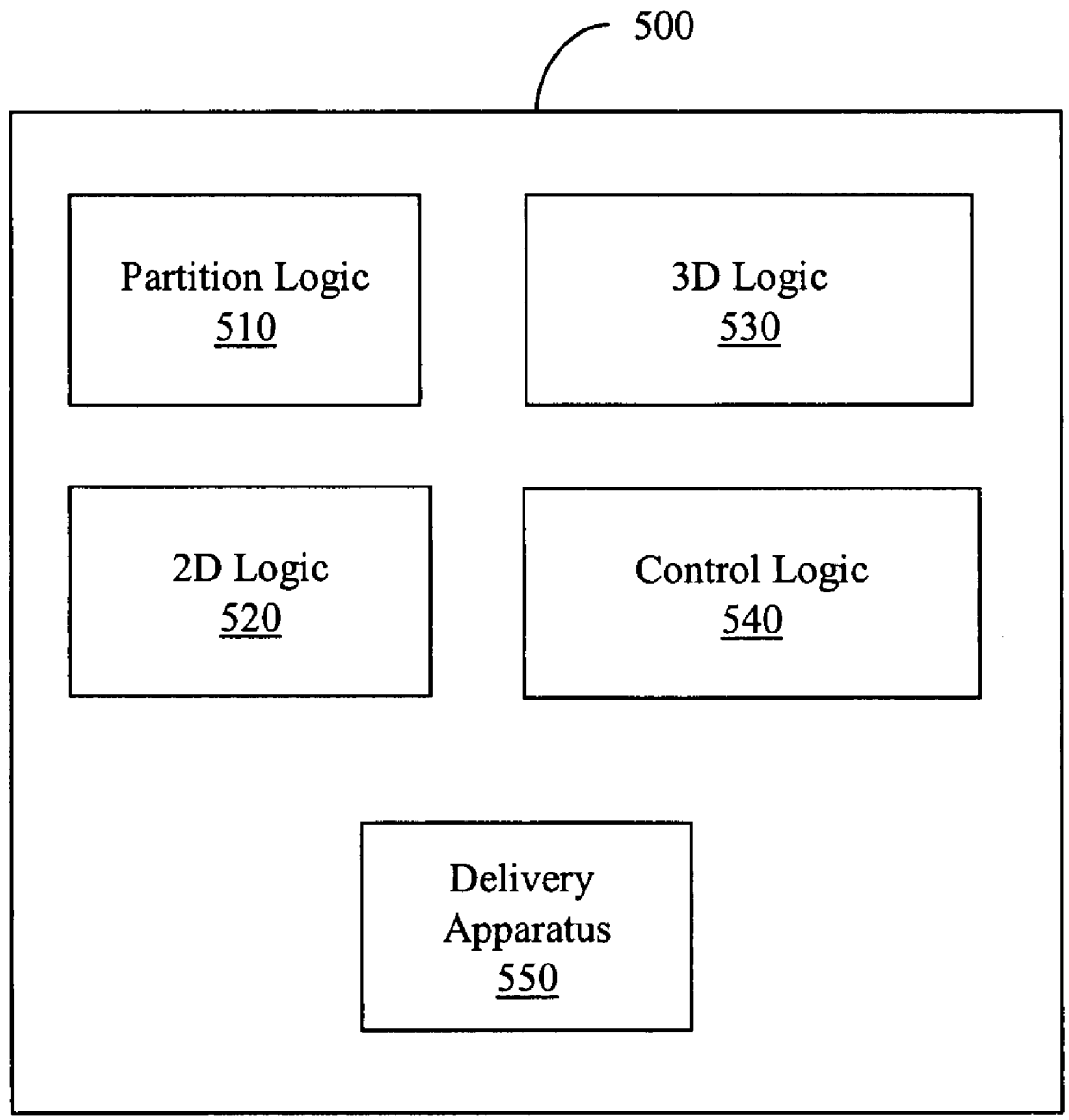
FIG. 5 illustrates an example apparatus associated with radiosurgery planning and delivery.

FIG. 5 illustrates an example apparatus 500 associated with Tomosurgery planning and delivery. Apparatus 500 includes elements similar to those described in connection with apparatus 400. For example, apparatus 500 includes a partition logic 510, a 2D logic 520, a 3D logic 530, and a control logic 540. Additionally, apparatus 500 includes a delivery apparatus 550. In one example the delivery apparatus 550 may be a modified Leksell Gamma Knife.

In one example, the delivery apparatus 550 may be a Linac unit with a collimator to shape radiation to a slit beam. The delivery apparatus 550 may include a ring-shaped secondary helmet with multiple collimator channels through which multiple beams can focus to an isocenter to form a disk-shaped shot. The delivery apparatus 550 may also include a robotic positioning system that connects a head frame to the ring-shaped secondary helmet. While a head frame and a "helmet" are described, it is to be appreciated that the delivery apparatus 550 may be modified to facilitate Tomosurgery to body parts other than the head. It is to be appreciated that delivery apparatus 550 may be other devices that are capable of producing a substantially planar shot and moving the isocenter of that shot through a treatment slice according to a 2D plan. For example, the delivery apparatus 550 may include a rotating secondary apparatus and/or may include elements to rotate a slit beam around a fixed portion of the delivery apparatus.

Since a radiation source(s) may decay, apparatus 500 may include a dosimeter to calibrate the delivery apparatus. In one example, the partition logic 510 may include a logic to receive a set of pre-operative images in which the target volume is represented. The partition logic 510 may then automatically partition the target volume into treatment slices.

Figure 6:
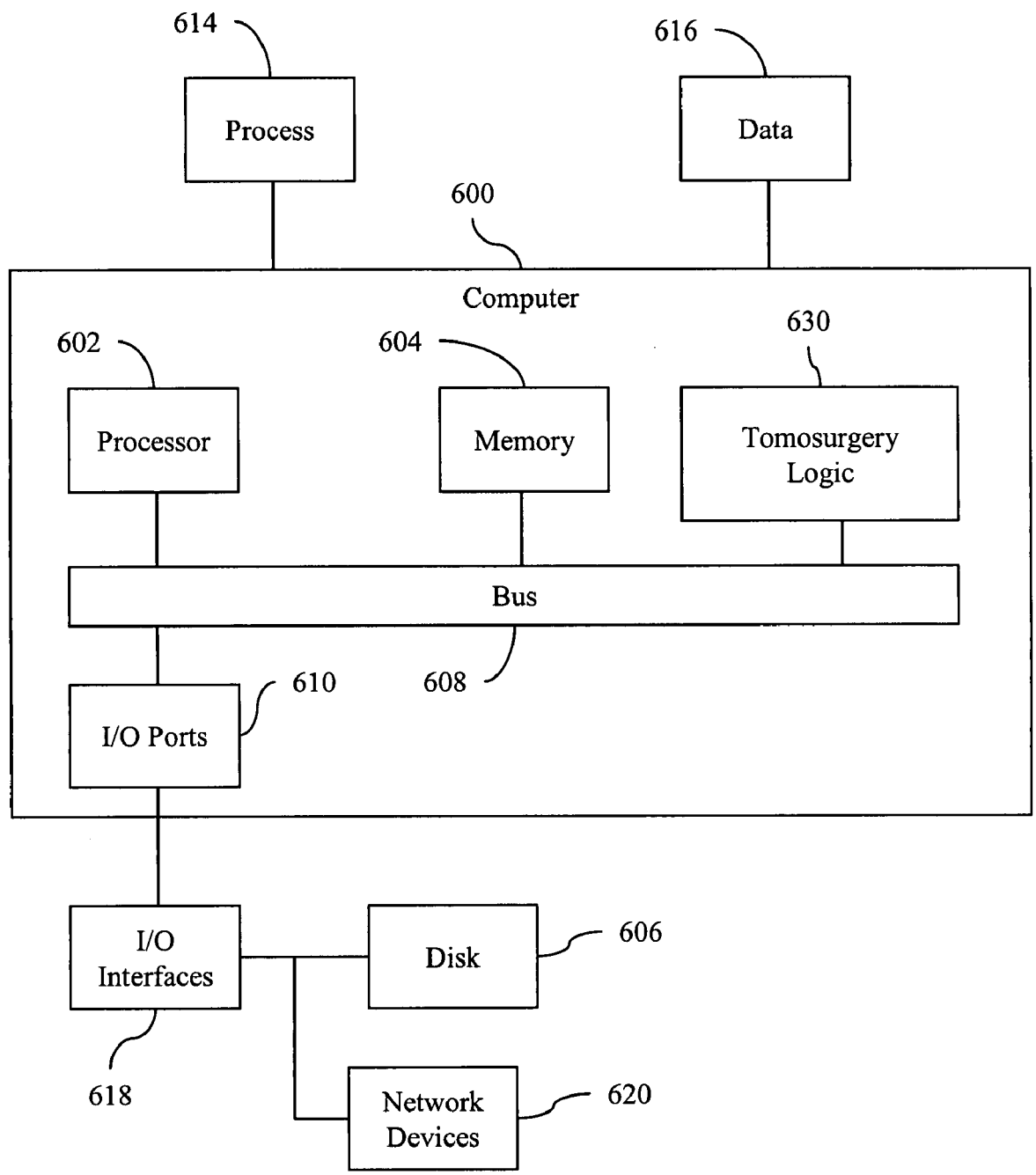
FIG. 6 illustrates an example computing environment in which example systems and methods illustrated herein may operate.

FIG. 6 illustrates an example computing device in which example systems and methods described herein, and equivalents, may operate. The example computing device may be a computer 600 that includes a processor 602, a memo 604, and input/output ports 610 operably connected by a bus 608. In one example, the computer 600 may include a Tomosurgery logic 630 configured to facilitate planning for Tomosurgery and delivering radiation according to a Tomosurgery plan. In different examples, the logic 630 may be implemented in hardware, software, firmware, and/or combinations thereof. Thus, the logic 630 may provide means (e.g., hardware, software, firmware) for identifying a set of treatment slices in a target volume and means (e.g., hardware, software, firmware) for planning a two dimensional path through a treatment slice. Logic 630 may also provide means (e.g., hardware, software, firmware) for assembling a three dimensional plan for performing radio-surgery on the target volume, and means (e.g., hardware, software, firmware) for controlling a radiosurgery delivery apparatus to move the intersection of the coplanar radiation beams through the target volume according to the three dimensional plan. While the logic 630 is illustrated as a hardware component attached to the bus 608, it is to be appreciated that in one example, the logic 630 could be implemented in the processor 602.

The means described in connection with logic 630 may determine an optimal slice thickness using the following inputs, algorithms, and outputs.

Input:

Calculated 3D dose kernel d of a disk-shaped shot.

Origin/center of d(x, y, z) set to (0, 0, 0).

Algorithm:

(1) Calculate the cross-sectional dose profile Dcs of the 3D dose bar by projecting d (x, y, z) to y-z plane. Here, Dcs is a function of y and z.

(2) Find the FWHM of Dcs(y=0, z).

Output:

The FWHM approximately equals to the optimal treatment slice thickness, Topt.

The means described in connection with logic 630 may interpolate the 3D volume data of segmented tumor and critical section (CS) using the following inputs, algorithms, and outputs.

Input:

Binary (BW) volume data of segmented tumor and CS, as Vt and Vcs respectively. Sizes of Vt and Vcs, Dim_t and Dim_cs, and their voxel sizes, VOXS_t and VOXS_cs. Real volume values.

Algorithm:

(1) Use cubic interpolation to resample Vt and Vcs to the smaller voxels, $0.25 \times 0.25 \times 0.25$ mm$^3$.→grayscale volume data, VI_t and VI_cs, which have the enlarged dimensions than the original volume sizes (Dim_t and Dim_cs).

(2) Use 3D smoothing kernel to smooth VI_t and VI_cs→VS_t and VS_cs.

(3) Find the best threshold TH_OPT where the thresholded tumor volume and CS volume close to the real volumes. The search of the best threshold can be performed through binary search approach:
 a. Testing the middle of an interval (initially 0-1)
 b. Eliminating a half of that interval
 c. Repeating the procedures a-c on the other half of that interval.
 Termination condition: the difference between the old and new threshold values<the pre-defined tolerance value.

(4) Perform thresholding on VI_t and VI_cs by using the threshold TH_OPT.

Output:

Binary volume data for resampled tumor and CS, VO_t and VO_cs.

The means described in connection with logic 630 may determine a raster scan format using the following inputs, algorithms, and outputs.

Input:

Tumor and CS volume data, VO_t, and VO_cs.

Tumor volume thickness T and the optimal treatment slice thickness Topt.

Algorithm:
(1) Based on equation T=Topt×N+R, calculate R and N.
(2) Divide the tumor volume along the z direction to a serial N adjacent treatment slices (with the thickness as Topt) starting from the superior side. The middle x-y plane of each treatment slice is the corresponding raster-scan plane. The locations of the raster-scan planes in z are recorded in an N-sized array, raster_z.
(3) If R=0, go to (4); otherwise, append a new entry onto the array raster_z (now, the array size becomes N+1). The value of new entry, raster_z(N+1)=raster_z(N)+R. The total number of the raster-scan planes is denoted as n (=N or N+1).
(4) For each treatment slice, project tumor tissues and CS tissues onto the corresponding raster-scan plane. The projected images are denoted as Proj_t and Proj_cs for tumor and CS tissues respectively.
(5) Place the raster lines within the tumor projection regions but not in the CS projection regions. Record the location of each raster-scan point into the array raster_points(x, y, z).

Output:

The locations of raster-scan points, raster_points array.

The means described in connection with logic 630 may perform a first stage optimization using the following inputs, algorithms, and outputs.

Input:

raster_points array.

Tumor and CS volume data, VO_t and VO_cs.

Prescribed dose for tumor, PRESCRIPTION_DOSE=1.

Dose tolerance of normal tissues (NT), TOLERANCE_NT=0.2.

Dose tolerance of CS, TOLERANCE_CS=0.2.

Important factors to tumor, NT, and CS, IF_T, IF_NT, and IF_CS.

Virtually adjusted prescribed dose, VPD (fixed to 0.8 here).

Algorithm:

$$\tau_j^{k+1} = \tau_j^k \left( \sum_{tissue} \sum_i I_i \cdot d_{ji} \cdot D_i^P \right) \cdot \left( \sum_{tissue} \sum_i I_i \cdot d_{ji} D_i^{d(k)} \right)^{-1}$$

(1) Calculate τ for raster points based on the iterative equation.
(2) Terminate iterative procedure when the tumor killing ratio becomes worse.

Output:

Array raster_weight, which records τ of each raster point.

The means described in connection with logic 630 may pre-process for the second stage optimization using the following inputs, algorithms, and outputs.

Input:

Arrays, raster_weight and raster_points.

Shot dose kernel d.

Algorithm:

For the i-th treatment slice:
 (1) Allocate computer memory DS(i) as a 3D matrix. DS(i) has the thickness of 3×Topt in z.
 (2) Calculate the 3D dose distribution resulted from the i-th planar raster scanning. The resulted dose distribution is saved into DS(i). The dose distribution is calculated based on 3D convolution of d and raster_weight.

Output:

Totally n DS matrices.

The means described in connection with logic 630 may perform a second stage optimization using the following inputs, algorithms, and outputs.

Input:

n DS matrices.

Arrays raster_weight and raster_points.

Tumor and CS volume data, VO_t and VO_cs.

Prescribed dose for tumor, PRESCRIPTION_DOSE=1.

Dose tolerance of normal tissues (NT), TOLERANCE_NT=0.2.

Dose tolerance of CS, TOLERANCE_CS=0.2.

Important factors to tumor, NT, and CS, IF_T, IF_NT, and IF_CS.

Virtually adjusted prescribed dose, VPD.

Algorithm:

$$w_i^{k+1} = w_i^k \left( \sum_{tissue} \sum_n I \cdot D_i^s \cdot D_f^P \right) \cdot \left( \sum_{tissue} \sum_n I_i \cdot D_i^s D_f^{d(k)} \right)^{-1}$$

(1) Calculate w for each treatment slice based on the iterative equation.
(2) Terminate iterative procedure when the tumor killing ratio and CS survival (if applicable) becomes worse.
(3) For each treatment slice, adjusting the shot speed:

raster_weight=raster_weight×w.

Output:

The adjusted raster_weight array. The adjusted shot weights (speed) can now be used to calculate the dose distribution of the final treatment plan.

Generally describing an example configuration of the computer 600, the processor 602 may be a variety of various processors including dual microprocessor and other multi-processor architectures. A memory 604 may include volatile memory and/or non-volatile memory. Non-volatile memory may include, for example, ROM, PROM, EPROM, and EEPROM. Volatile memory may include, for example, RAM, synchronous RAM (SRAM), dynamic RAM (DRAM), synchronous DRAM (SDRAM), double data rate SDRAM (DDR SDRAM), and direct RAM bus RAM (DRRAM).

A disk 606 may be operably connected to the computer 600 via, for example, an input/output interface (e.g., card, device) 618 and an input/output port 610. The disk 606 may be, for example, a magnetic disk drive, a solid state disk drive, a floppy disk drive, a tape drive, a Zip drive, a flash memory card, and/or a memory stick. Furthermore, the disk 606 may be a CD-ROM, a CD recordable drive (CD-R drive), a CD rewriteable drive (CD-RW drive), and/or a digital video ROM drive (DVD ROM). The memory 604 can store a process 614 and/or a data 616, for example. The disk 606 and/or the memory 604 can store an operating system that controls and allocates resources of the computer 600.

The bus 608 may be a single internal bus interconnect architecture and/or other bus or mesh architectures. While a single bus is illustrated, it is to be appreciated that the computer 600 may communicate with various devices, logics, and peripherals using other busses (e.g., PCIE, SATA, Infiniband, 1394, USB, Ethernet). The bus 608 can be types including, for example, a memory bus, a memory controller, a peripheral bus, an external bus, a crossbar switch, and/or a local bus.

The computer 600 may interact with input/output devices via the i/o interfaces 618 and the input/output ports 610. Input/output devices may be, for example, a keyboard, a microphone, a pointing and selection device, cameras, video cards, displays, the disk 606, the network devices 620, and so on. The input/output ports 610 may include, for example, serial ports, parallel ports, and USB ports.

The computer 600 can operate in a network environment and thus may be connected to the network devices 620 via the i/o interfaces 618, and/or the i/o ports 610. Through the network devices 620, the computer 600 may interact with a network. Through the network, the computer 600 may be logically connected to remote computers. Networks with which the computer 600 may interact include, but are not limited to, a local area network (LAN), a wide area network (WAN), and other networks.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A computer-implemented method, comprising:
    logically dividing a target volume into two or more treatment slices to be radiated individually by radiation delivered by co-planar beams;
    planning a two dimensional path for moving a shaped isocenter through a treatment slice, the two dimensional path to include a set of scan points to be visited by the isocenter, the isocenter to be produced by the intersection of the co-planar beams, and where planning a first two dimensional path through a first treatment slice can begin before a second treatment slice has been defined;
    planning a three dimensional path for moving the shaped isocenter through the target volume based) at least in part, on two or more of the two dimensional paths; and
    providing a signal to control a radiosurgery device to deliver radiation using the coplanar beams to the target volume based, at least in part, on the three dimensional path.

2. The method of claim 1, including receiving one or more pre-operative images in which at least a portion of the target volume appears, the pre-operative images being one or more of, magnetic resonance images, computed tomography images, and x-ray images.

3. The method of claim 2, including fixing one or more fiducial markers at a position relative to the target volume, where the pre-operative images are to include representations of the one or more fiducial markers; and
    where assembling, the three dimensional plan depends, at least in part, on a relationship between an image of a fiducial in a first treatment slice and an image of a fiducial in a second treatment slice.

4. The method of claim 2, including fixing one or more fiducial markers at a position relative to the target volume, where the pre-operative images are to include representations of the one or more fiducial markers; and
    where the delivery device is controlled, at least in part, on determining a relationship between a portion of the target volume and one or more of, a collimator opening, and a radiation source.

5. The method of claim 1, where logically dividing the target volume into two or more treatment slices includes determining a treatment slice thickness.

6. The method of claim 1, a two dimensional path being a raster scan path.

7. The method of claim 1, the shaped isocenter having a disk shape.

8. The method of claim 1, where a shot weight produced by the radiation delivered by the coplanar beams is modulated by controlling the movement of the isocenter.

9. The method of claim 8, where the shot weight is modulated by controlling one or more of, a number of coplanar beams applied to the target volume, a hole size in a collimator through which at least one of the coplanar beams is to pass, and a temporal delay between one or more of the coplanar beams being applied to the target volume.

10. The method of claim 1, where planning a two dimensional path through a treatment slice includes calculating a resulting dose according to:

$$D^d = d * \tau \Rightarrow D^d(x, y) = \sum_m \sum_n d(m - x, n - y)\tau(m, n),$$

where D represents the resulting dose;
where d represents the disk-shaped shot dose kernel;
where $\tau$ represents a time series variable that represents the time it takes a moving shot to pass through a unit length of a raster line;
where m represents a first index associated with a raster line scan point position; and
where n represents a second index associated with a raster line scan point position.

11. The method of claim 10, where planning a two dimensional path through a treatment slice includes solving for $\tau$ according to:

$$O(\overline{\tau}) = \sum_{tissue} \sum_i I_i(D_i^P - D_i^d)^2 = \sum_{tissue} \sum_i I_i\left(D_i^P - \sum_j d_{ji}\tau_j\right)^2,$$

where $D_i^P$ is the prescribed dose for the tumor;
$D_i^P$ is the planned dose distribution to be optimized; and $d_{ji}$ of the dose kernel represents the dose contribution to the $i^{th}$ spatial location while the shot moves through the $j^{th}$ scan point.

12. The method of claim 11, where assembling the three dimensional plan includes solving for a final three-dimensional plan dose according to:

$$D_f = \sum_n w_i \cdot D_i^s$$

where $D_i^S$ is the 3D dose matrix; and
$w_i$ is the weight assigned to the $i^{th}$ single-plane raster scan.

13. The method of claim 1, where two dimensional paths through two or more treatment slices are to be planned substantially in parallel.

14. The method of claim 1, where two dimensional paths through two different treatment slices differ in at least one of, scan pattern, importance weighted quadratic objective function, and slice orientation.

15. The method of claim 1, including controlling a delivery apparatus to deliver a set of coplanar beams according to the three dimensional plan.

16. The method of claim 15, including controlling the delivery apparatus to deliver the coplanar beams to two or more treatment slices substantially in parallel.

17. The method of claim 15, including:
calibrating the delivery apparatus before controlling the delivery apparatus to deliver the coplanar beams; and
controlling the delivery apparatus based, at least in part, on the calibration.

18. The method of claim 17, where calibrating the delivery apparatus includes acquiring a signal from a polymer gel-MRI dosimeter to which the delivery apparatus applied a set of coplanar beams.

19. The method of claim 1, including changing a tumor prescription dose between planning a set of two dimensional paths and planning the three dimensional path.

20. The method of claim 1, including dynamically altering the size of a collimator hole through which at least one beam will pass during radiation delivery to perform one or more of, modulating shot weight, and controlling isocenter location.

21. The method of claim 1, including selecting a delivery apparatus to deliver the coplanar beams based, at least in part, on the three dimensional plan.

22. The method of claim 1 where planning the two dimensional path includes considering a three dimensional dose bar interaction within a treatment slice and where assembling the three dimensional path includes considering a three dimensional dose bar interaction between treatment slices.

23. A machine-readable medium having stored thereon machine executable instructions that if executed by a machine cause the machine to perform a method, the method comprising:
receiving one or more pre-operative images in which at least a portion of a target volume to be radiated appears, the pre-operative images being one or more of, magnetic resonance images, computed tomography images, and x-ray images;
determining a treatment slice thickness;
logically dividing the target volume into two or more treatment slices to be radiated individually by radiation delivered by co-planar beams, the treatment slices having the treatment slice thickness;
planning a two dimensional path for moving a disk-shaped isocenter through a treatment slice, the two dimensional path to include a set of scan points to be visited by the isocenter, the isocenter to be produced by the intersection of the co-planar beams, the two dimensional path being a raster scan path, where two dimensional paths through two or more treatment slices are to be planned substantially in parallel;
planning a three dimensional path for moving the shaped isocenter through the target volume based, at least in part, on two or more of the two dimensional paths, where a shot weight produced by the coplanar beams is modulated by controlling the movement of the isocenter;
providing a signal to control a radiosurgery device to deliver radiation using the coplanar beams to the target volume based, at least in part, on the three dimensional path; and
controlling a delivery apparatus to deliver a set of coplanar beams according to the three dimensional plan,
where planning the two dimensional path includes considering a three dimensional dose bar interaction within a treatment slice and where assembling the three dimensional path includes considering a three dimensional dose bar interaction between treatment slices.

24. A radio surgical treatment method, comprising:
identifying a set of two dimensional paths through a set of treatment slices, where planning a first two dimensional path through a first treatment slice can begin before a second treatment slice has been defined;
receiving a treatment plan comprising a three dimensional path through a target volume based, at least in part, on the set of two dimensional paths;
controlling a radio surgical apparatus to generate a disk-shaped shot having an isocenter and to continuously adjust the isocenter location to produce a coplanar shot movement through the three dimensional path; and
controlling the radio surgical apparatus to modulate the speed at which the isocenter location moves.

25. The method of claim 24, where modulating the speed at which the isocenter location is moved includes controlling one or more robotic apparatus associated with the radio surgical apparatus to reposition one or more of, a patient, the radio surgical apparatus, and a radiation source.

26. An apparatus, comprising:
a first logic to partition a target volume into a set of treatment slices, the target volume representing a tissue to be subjected to radiation delivered by a set of coplanar beams;
a second logic to determine a set of two dimensional raster scanning paths through the set of treatment slices, where determining a first two dimensional raster scanning path through a first treatment slice can begin before a second treatment slice has been defined;
a third logic to determine a three dimensional path to irradiate the target volume to within a pre-determined dose, the three dimensional path being based, at least in part, on the set of two dimensional raster scanning paths; and
a fourth logic to control a delivery apparatus to deliver a set of coplanar beams to the target volume in accordance with the three dimensional path.

27. The apparatus of claim 26, the delivery apparatus being a modified Leksell Gamma Knife.

28. The apparatus of claim 26, the delivery apparatus comprising:
- a Linac unit with a collimator to shape radiation to a slit beam;
- a ring-shaped secondary helmet with multiple collimator channels through which multiple beams can focus to an isocenter to form a disk-shaped shot; and
- a robotic positioning system that connects a head frame to the ring-shaped secondary helmet.

29. The apparatus of claim 26, the delivery apparatus including a rotating secondary apparatus.

30. The apparatus of claim 26, the delivery apparatus to rotate a slit beam around a fixed portion of the delivery apparatus.

31. The apparatus of claim 26, including the delivery apparatus.

32. The apparatus of claim 31, including a dosimeter to calibrate the delivery apparatus.

33. The apparatus of claim 32, the first logic to receive a set of pre-operative images in which the target volume is represented.

34. A system, comprising:
- means for identifying a set of treatment slices in a target volume;
- means for planning a two dimensional path through a treatment slice for a focused isocenter produced by the intersection of coplanar radiation beams, where planning a first two dimensional path through a first treatment slice can begin before a second treatment slice has been defined;
- means for assembling a three dimensional plan for performing radiosurgery on the target volume, where the three dimensional plan depends, at least in part, on a set of two dimensional paths through treatment slices; and
- means for controlling a radiosurgery delivery apparatus to move the intersection of the coplanar radiation beams through the target volume according to the three dimensional plan.

* * * * *

UNITED STATES PATENT AND TRADEMARK OFFICE
CERTIFICATE OF CORRECTION

PATENT NO. : 7,616,735 B2  Page 1 of 2
APPLICATION NO. : 11/728927
DATED : November 10, 2009
INVENTOR(S) : Maciunas et al.

It is certified that error appears in the above-identified patent and that said Letters Patent is hereby corrected as shown below:

Detailed Description:

In column 5, line 4, delete "approached" and insert --approach--.

In column 5, line 65, delete "combinations" and insert --combination(s)--.

In column 9, equation (1), delete "$$D(x,y,z) = d \otimes \frac{1}{v} = \sum_{x'} d(x-x',x,y,z)(1/v(x'))$$"

and insert --$$D(x,y,z) = d \otimes \frac{1}{v} = \sum_{x'} d(x-x',y,z)(1/v(x'))$$--.

In column 10, equation (4), delete : "$$\kappa(z) = \left| \frac{\frac{\partial H_{l_0}(z)}{\partial^2 z}}{\left(1+\left(\frac{\partial H_{l_0}(z)}{\partial z}\right)^2\right)^{3/2}} \right|$$"

and insert --$$\kappa(z) = \left| \frac{\frac{\partial^2 H_{l_0}(z)}{\partial^2 z}}{\left(1+\left(\frac{\partial H_{l_0}(z)}{\partial z}\right)^2\right)^{3/2}} \right|$$--.

In column 10, line 23, delete "straight vanishes" and insert --straight line vanishes--.

In column 21, line 53, delete "memo" and insert --memory--.

In column 21, line 66, delete "radio-surgery" and insert --radiosurgery--.

CERTIFICATE OF CORRECTION (continued)
U.S. Pat. No. 7,616,735 B2

Detailed Description:

In column 24, line 30, delete " $$w_i^{k+1} = w_i^k \left( \sum_{tissue} \sum_n I \cdot D_i^s \cdot D_f^p \right) \cdot \left( \sum_{tissue} \sum_n I_l \cdot D_i^s \cdot D_f^{d(k)} \right)^{-1}$$ "

and insert -- $$w_i^{k+1} = w_i^k \left( \sum_{tissue} \sum_n I \cdot D_i^s \cdot D_f^p \right) \cdot \left( \sum_{tissue} \sum_n I \cdot D_i^s \cdot D_f^{d(k)} \right)^{-1}$$ --.

Claims:

In column 25, line 62, claim 1, delete "based)" and insert --based,--.

In column 26, line 67, claim 11, delete "$D_i^p$" and insert --$D_i^d$--.

Signed and Sealed this

Nineteenth Day of January, 2010

David J. Kappos
*Director of the United States Patent and Trademark Office*